US007599734B2

(12) United States Patent (10) Patent No.: US 7,599,734 B2
Naruse (45) Date of Patent: Oct. 6, 2009

(54) ELECTRONIC ENDOSCOPE SYSTEM

(75) Inventor: Masato Naruse, Hachioji (JP)

(73) Assignee: Olympus Corporation (JP)

(*) Notice: Subject to any disclaimer, the term of this patent is extended or adjusted under 35 U.S.C. 154(b) by 696 days.

(21) Appl. No.: 11/188,918

(22) Filed: Jul. 25, 2005

(65) Prior Publication Data
US 2006/0020168 A1 Jan. 26, 2006

(30) Foreign Application Priority Data
Jul. 26, 2004 (JP) .............................. 2004-217882

(51) Int. Cl.
*A61B 5/04* (2006.01)
(52) U.S. Cl. ..................................................... 600/514
(58) Field of Classification Search ................. 600/178, 600/514; 606/31; 372/32
See application file for complete search history.

(56) References Cited

U.S. PATENT DOCUMENTS 4,730,323 A * 3/1988 Seaton ........................ 372/32
4,744,359 A * 5/1988 Hatta et al. .................... 606/31
6,730,019 B2 * 5/2004 Irion .......................... 600/178

FOREIGN PATENT DOCUMENTS

| JP | 10-216085 | 8/1998 |
| JP | 2000-089130 | 3/2000 |
| JP | 2001-061777 | 3/2001 |

* cited by examiner

*Primary Examiner*—George Manuel
(74) *Attorney, Agent, or Firm*—Ostrolenk Faber LLP

(57) ABSTRACT

An electronic endoscope system with high operability and high observing performance capable of driving properly and automatically the light-emitting elements without the size increase in system is provided, even in the case of using a plurality of interchangeable optical adaptors having varied numbers of light-emitting elements. A plurality of optical adaptors having LEDs are detachable to the distal end of an insertion unit of an endoscope. The insertion unit has an inserted electric cable connected to the LEDs. A constant-current circuit of an LED driving circuit flows constant current to the LEDs via the electric cable.

9 Claims, 6 Drawing Sheets

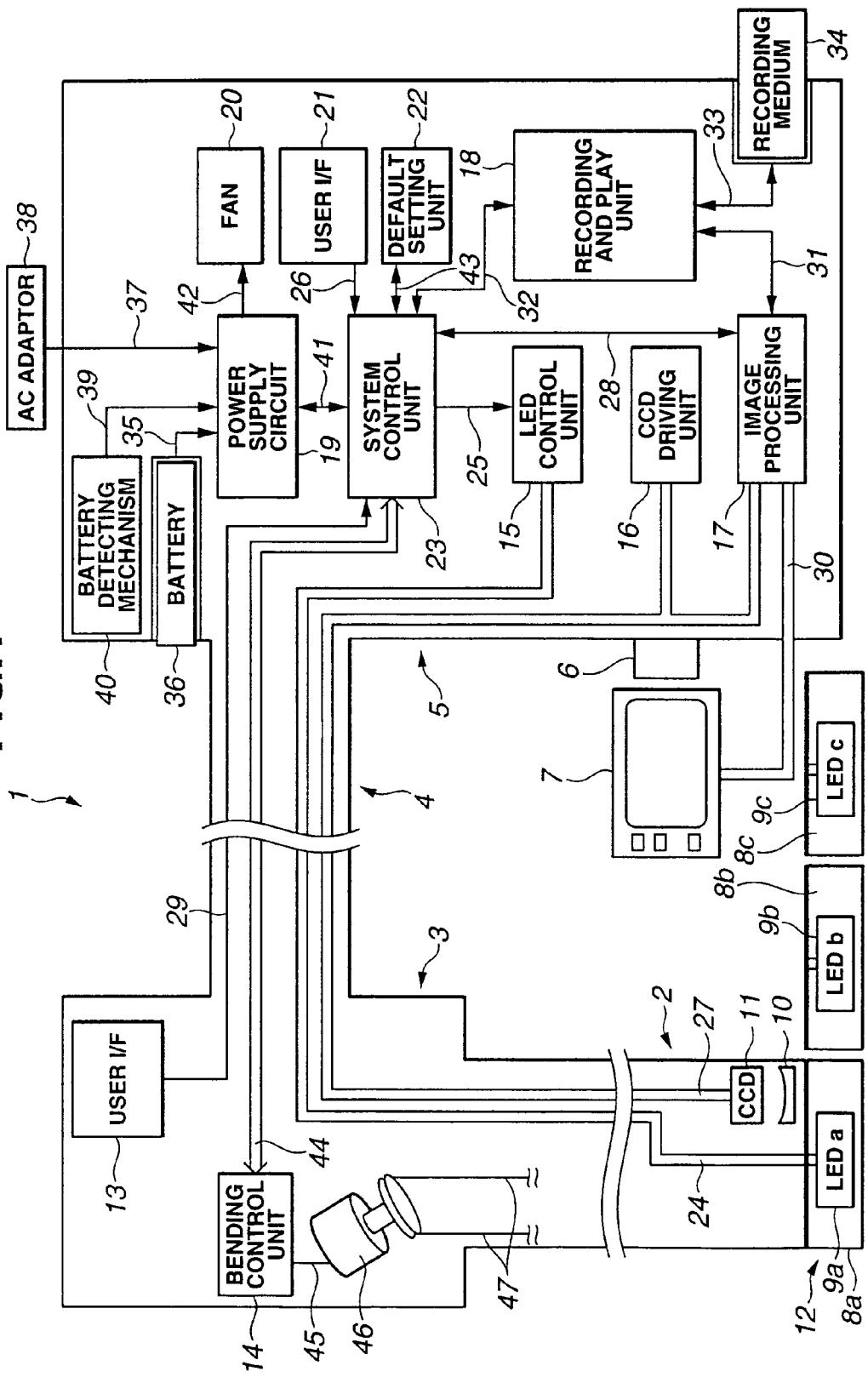

ical adaptor (refer to, e.g., Japanese Unexamined Patent Application Publication No. 2001-61777).

ELECTRONIC ENDOSCOPE SYSTEM

This application claims benefit of Japanese Application No. 2004-217882 filed on Jul. 26, 2004, the contents of which are incorporated by this reference.

BACKGROUND OF THE INVENTION

1. Field of the Invention

The present invention relates to an electronic endoscope system, and more particularly, to an electronic endoscope system in which an optical adaptor having illuminating means is attached to the distal end of an insertion unit.

2. Description of the Related Art

Recently, an endoscope system has widely been used. The endoscope system observes the organ in the body cavity by inserting an elongated insertion unit into the body cavity, and performs various treatments by using a treatment tool inserted in a treatment tool channel if necessary. Further, in the industrial field, the endoscope device observes and inspects the inner scratch or corrosion of a boiler, turbine, engine, and chemical plant.

In the above-mentioned endoscope system, since a dark portion, such as the body cavity, is often observed and the brightness in the observation therefore needs to be ensured. Then, an electronic endoscope system is widely used in which a light-emitting device, such as a lamp or an LED, is arranged, as illuminating means, at the distal portion of the insertion unit, and a subject is observed by an image pickup device, such as a CCD while illuminating the subject by the illuminating means.

Recently, the observed portion is complicated and is varied in accordance with the development of the endoscope medical field. The medical stuff requires an electronic endoscope system having illuminating means corresponding to the observed portion and an image pickup device with the pixel array (e.g., difference in pixel size or NTSC or PAL). Therefore, the diameter dimension of a pipe, serving as an observed target, is varied, e.g., large to small in the industrial electronic endoscope system and various optical adaptors corresponding to the diameter dimension or inspection target are prepared for various inspections.

Conventionally, a system using an interchangeable optical adaptor including an LED is proposed, as an electronic endoscope system having an interchangeable optical adaptor. For example, the electronic endoscope system has an interchangeable adaptor in which a plurality of LEDs, serving as illuminating means, are arranged near an objective lens, and further has a mechanism for supplying the power to the LED in the main body of the electronic endoscope. The contact on the proximal end of the interchangeable optical adaptor is connected to the contact of the distal end of the endoscope insertion unit, thereby driving the LEDs included in the interchangeable optical adaptor (refer to, e.g., Japanese Unexamined Patent Application Publication No. 10-216085 and Japanese Unexamined Patent Application Publication No. 2000-89130).

Further, the electronic endoscope system comprises an interchangeable optical adaptor having a plurality of LEDS, serving as illuminating means and a CMOS image sensor, serving as an image pickup device, and further an operating unit having a circuit for supplying the power to the LEDs and the CMOS image sensor. A connecting unit arranged to the proximal end of the interchangeable optical adaptor is connected to a connecting unit arranged to the distal end of an endoscope insertion unit, thereby driving the LEDs included

SUMMARY OF THE INVENTION

According to the present invention, an electronic endoscope system comprises: a plurality of optical adaptors having light-emitting elements, serving as illuminating means; an insertion unit to which the optical adaptors are freely detachably attached at the distal portion thereof and has an electric cable inserted thereto connected to the light-emitting elements; and a control unit having a constant-current circuit that sets, to be constant, the amount of current flowing to the light-emitting element via the electric cable.

BRIEF DESCRIPTION OF THE DRAWINGS

FIG. 1 is a block diagram schematically showing the entire structure of an electronic endoscope system according to an embodiment of the present invention;

DETAILED DESCRIPTION OF THE PREFERRED EMBODIMENTS

Figure 2A:
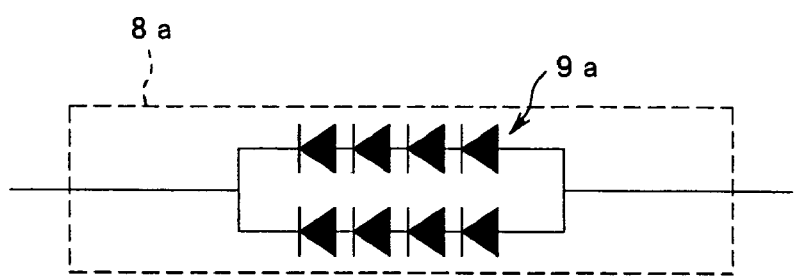
FIGS. 2A to 2C are explanatory diagrams of one structure of LEDs.

Hereinafter, a description is given of an embodiment of the present invention with reference to the drawings.

First, a description is given of the entire structure of an electronic endoscope system according to the embodiment of the present invention with reference to FIG. 1. FIG. 1 is block diagram schematically showing the entire structure of the electronic endoscope system according to the embodiment of the present invention. Referring to FIG. 1, an electronic endoscope system 1 according to the embodiment comprises: an insertion unit 2 that is elongated with flexibility; an operating unit 3 that is positioned at the proximal end of the insertion unit 2 and performs the bending operating of the insertion unit 2 and the like; a universal cable 4 that is extended from the operating unit 3 and is thicker in diameter than the insertion unit 2; a power supply unit (main body unit) 5 connected to the proximal end of the universal cable 4; a fixing unit 6 that is arranged to one side surface of the power supply unit 5; and a display device 7 detachable to the power supply unit 5 by using the fixing unit 6.

The insertion unit 2 comprises: an interchangeable optical adaptor 8a including light-emitting diodes (hereinafter, referred to as LEDs) 9a, serving as light-emitting devices as illuminating means for illuminating the observed portion; an objective lens 10 that forms an image of reflection light from the observed portion; and a charge-coupled device (hereinafter, referred to as a CCD) 11, serving as a solid-state image pickup device, that photoelectrically converts the reflection light whose image is formed by the objective lens 10 at the distal end. The interchangeable optical adaptor 8a is detachable to the distal end of the insertion unit 2 via a connecting unit 12, and is interchangeable to an interchangeable optical adaptor 8b including LEDs 9b and an interchangeable optical adaptor 8c including the LEDs 9c. Here, a description is given of the structures of the LEDs 9a to 9c with reference to FIGS. 2A to 2C.

Figure 2B:
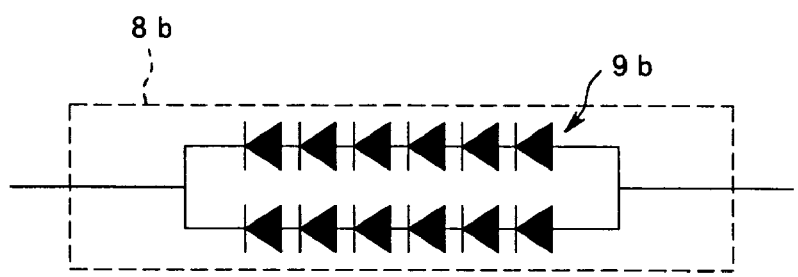
Figure 2C:
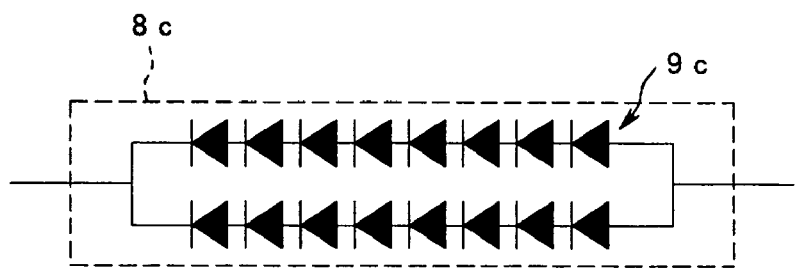

FIGS. 2A to 2C are explanatory diagrams of the structures of the LEDs 9a to 9c. Referring to FIG. 2A, the LEDs 9a comprise eight LEDs, and is structured by connecting, in parallel, two arrays each comprising four serially-connected LEDs. Referring to FIG. 2B, the LEDs 9b comprise twelve LEDs, and is structured by connecting, in parallel, two arrays each comprising six serially-connected LEDs. Referring to FIG. 2C, the LEDs 9c comprise sixteen LEDs, and is structured by connecting, in parallel, two arrays each comprising eight serially-connected LEDs. That is, the number of parallel arrays is two in the LEDs 9a to 9c and, however, the number of LEDs serially-connected to the arrays is 4, 6, and 8 in the LEDs 9a to 9c, respectively. In other words, the numbers of parallel arrays are equal in the LEDs 9a to 9c, and the numbers of LEDs serially-connected are different from each other in the LEDS 9a to 9c.

The operating unit 3 comprises: a first user interface 13 that inputs a signal for controlling the operation of units in the electronic endoscope system 1; and a bending control unit 14 that controls the bending operation of the distal portion of the insertion unit 2.

The power supply unit 5 comprises: an LED control unit 15 that supplies constant current corresponding to the LEDs 9a to 9c and controls the turn-on/turn-off operation; a CCD driving unit 16 that drives the CCD 11; an image processing unit 17 that processes an image signal photoelectrically-converted by the CCD 11 and creates an observed image; a recording and play unit 18 that records the observed image and plays the recorded observed image; a power supply circuit 19; a fan 20 that cools the inside of the power supply unit 5; a second user interface 21 that inputs a signal for controlling the operation of the units in the electronic endoscope system 1 by a user; a default setting unit 22; and a system control unit 23 that outputs a control signal to the units in accordance with the signal inputted from the second user interface 21.

The LED control unit 15 is electrically connected to the LEDs 9a by a cable 24. That is, upon the interchangeable optical adaptor 8a being attached to the distal portion of the insertion unit 2 the LEDs 9a are electrically connected, by the connecting unit 12, to the cable 24 extended to the connecting unit 12 at the distal end of the insertion unit 2 from the LED control unit 15. Upon attaching the interchangeable optical adaptor 8b or the interchangeable optical adaptor 8c to the distal end of the insertion unit 2, similarly, the LEDs 9b are electrically connected to the cable 24, or the LEDs 9c are electrically connected to the cable 24 in the connecting unit 12.

The LED control unit 15 is also electrically connected to the system control unit 23 via a cable 25. The system control unit 23 is electrically connected to the second user interface 21 via a cable 26. The user inputs the signal for controlling the turn-on/turn-off operation of the LEDs 9a from the second user interface 21. When the second user interface 21 is a switch, the turn-on/turn-off operation of the LEDs 9a is controlled by switching the on/off operation of the switch. The system control unit 23 outputs a control signal of turn-on/turn-off operation of the LEDs 9a to the LED control unit 15 in accordance with the signal inputted from the second user interface 21. The LED control unit 15 turns on/off the LEDs 9a in accordance with the signal received from the system control unit 23. Upon attaching the interchangeable optical adaptor 8b or the interchangeable optical adaptor 8c to the distal end of the insertion unit 2, the LED control unit 15 turns on/off the LEDS 9b or LEDS 9c in accordance with the signal received from the system control unit 23. The internal structure of the LED control unit 15 will specifically be described later.

An image of the reflection light from the observed portion is formed to the CCD 11 via the objective lens 10 by the illumination of the LEDs 9a during turning-on the LEDs 9a. Here, the CCD 11 is electrically connected to a CCD driving unit 16 via a complex coaxial cable 27, and receives a signal for driving the CCD 11 from the CCD driving unit 16. The CCD 11 photoelectrically converts the formed observed image of the observed portion at the timing based on the signal received from the CCD driving unit 16. The photoelectrically-converted image signal is outputted to an image processing unit 17 that is electrically connected to the CCD 11 via a complex coaxial cable 27.

The image processing unit 17 is electrically connected to the system control unit 23 via a cable 28. The system control unit 23 is electrically connected to the first user interface 13 via a cable 29. The user inputs, from the first user interface 13, various instructions, such as zoom-up, zoom-down, and freeze. For example, when the first user interface 13 is a switch, the user inputs various instructions, such as zoom-up, zoom-down, and freeze by the button operation of the switch. The system control unit 23 outputs, to the image processing unit 17, a signal for issuing instructions, such as zoom-up, zoom-down, and freeze. The image processing unit 17 processes an image signal in accordance with the signal received from the system control unit 23, and creates the observed image. The observed image is outputted and displayed out, via a coaxial cable 30, to the display device 7 that is electrically connected to the image processing unit 17.

Further, the image processing unit 17 outputs, to the display device 7, the observed image that is recorded in advance, in addition to the observed image that is obtained by processing and creating the image signal outputted from the CCD 11. The recording and play of the observed image are performed by a recording and play unit 18 that is electrically connected to the image processing unit 17 via a cable 31.

The recording and play unit 18 is electrically connected to the system control unit 23 via a cable 32, and is operated by receiving a signal for recording the observed image and playing the observed image from the system control unit 23. Upon receiving the signal for recording the observed image from the system control unit 23, the recording and play unit 18 receives, via a cable 31, the observed image that is created by the image processing unit 17. The received observed image is outputted and is stored to a recording medium 34 that is electrically connected to the recording and play unit 18 via a transfer line 33 and stores the observed image. Upon receiving the signal for instructing the play of the recorded observed image from the system control unit 23, the recording and play unit 18 reads out, via the transfer line 33, the observed image stored in the recording medium 34. The read observed image is outputted to the image processing unit 17 from the recording and play unit 18 and is then outputted and displayed out to the display device 7 via the coaxial cable 30 from the image processing unit 17.

The power supply circuit 19 is electrically connected to a battery 36 via a cable 35, and is electrically connected to an AC adaptor 38 via a cable 37. A voltage is applied from the battery 36 or the AC adaptor 38, thereby generating an internal applying voltage for driving the units in the electronic endoscope system 1. The output from the battery 36 and the output from the AC adaptor 38 are coupled by a diode (not shown), and a voltage is supplied to the power supply circuit 19 only from one of the outputs with a higher voltage. An internal supplied voltage generated by the power supply circuit 19 is supplied to the units in the electronic endoscope system 1 from the power supply circuit 19 via a cable (not shown).

The power supply circuit 19 is electrically connected to a battery detecting mechanism 40 via a cable 39. The battery detecting mechanism 40 checks whether or not the battery 36 exists, and outputs the information thereon to the power supply circuit 19. The power supply circuit 19 outputs the received information on the presence or absence of battery to the system control unit 23 that is electrically connected via a cable 41.

The fan 20 is electrically connected to the power supply circuit 19 via a cable 42, and is driven by a voltage supplied from the power supply circuit 19 via the cable 42 and cools the inside of the power supply unit (main body) 5.

The second user interface 21 is electrically connected to the system control unit 23 via the cable 26, and outputs, to the system control unit 23, a signal for controlling the operation of the units in the electronic endoscope system 1, inputted from the user. The default setting unit 22 is electrically connected to the system control unit 23 via a cable 43.

The system control unit 23 is electrically connected to the bending control unit 14 via a cable 44 passing through the universal cable 4. The bending control unit 14 is electrically connected to a motor 46 via a cable 45, and drives and stops the motor 46, thereby controlling the bending operation of the distal portion of the insertion unit 2. The details of the control for bending operation is as follows. That is, the user inputs instructions for driving or stopping the motor 46 from the second user interface 21. For example, when the second user interface 21 is a switch, the user instructs the driving or stop of the motor 46 by the button operation of the switch. The system control unit 23 outputs, to the bending control unit 14, the signal for instructing the driving/stop of the motor 46 in accordance with the signal inputted from the second user interface 21. The bending control unit 14 drives or stops the motor 46 in accordance with the received signal.

A wire 47 comes into contact with a transmitting unit for transmitting the rotating force of the motor 46, e.g., a pulley, when the user brings down a joystick.

The user brings down the joystick (not shown) in the desired bending direction of the distal end of the insertion unit 2 while the motor 46 is driven. Thus, the wire 47 comes into contact with the transmitting unit of the rotating force of the motor 46, and the power of the motor 46 is transmitted to the wire 47, thereby bending the distal end of the insertion unit 2. The bending control unit 14 monitors the load of the connected motor 46, upon detecting an abnormal load to the motor 46, outputs, to the system control unit 23, a motor overload detecting signal. The system control unit 23 receives the motor overload detecting signal and then outputs a signal for instructing the stop of the motor 46 to the bending control unit 14 in order to prevent the failure of the system. The bending control unit 14 stops the motor 46 in accordance with the received signal.

Figure 3:
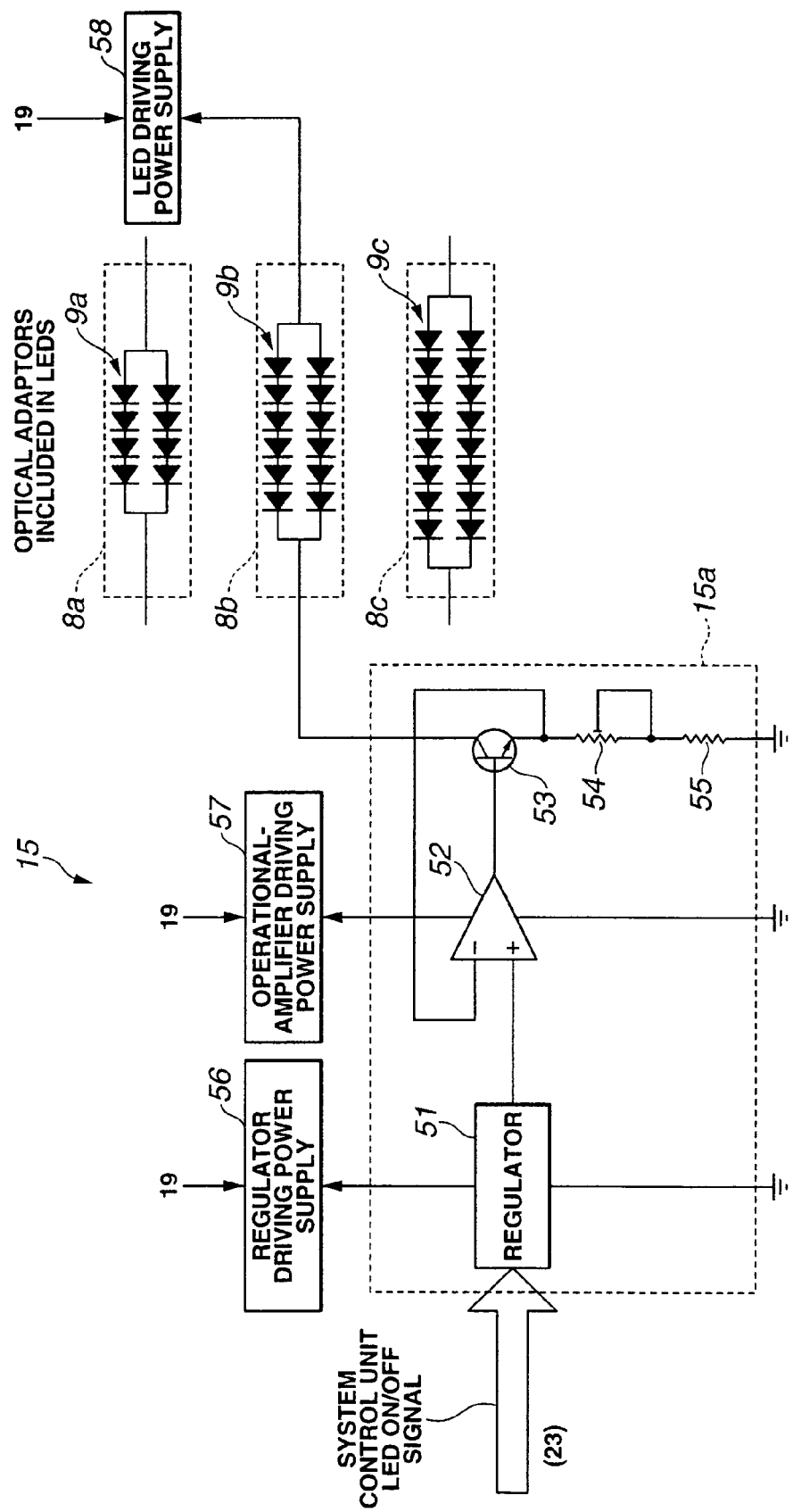
FIG. 3 is a circuit diagram for explaining one circuit structure in an LED control unit.

The description is given of the entire structure of the electronic endoscope system 1 according to the embodiment. Further, a detailed description is given of the internal circuit structure of the LED control unit 15 with reference to FIG. 3. FIG. 3 is an explanatory diagram of the internal circuit structure of the LED control unit 15. Here, a description is given of the case where the interchangeable optical adaptor 8b is attached to the distal end of the insertion unit 2.

The LED control unit 15 comprises a constant-current circuit 15a comprising: a regulator 51; an operational amplifier 52; a transistor 53; a variable resistor 54; and a fixed resistor 55. The regulator 51 receives a signal for controlling the turn-on/turn-off of the LEDs 9b from the system control unit 23 and drives, and controls the current supplied to the LEDs 9b by the transistor 53 via the operational amplifier 52 electrically-connected to the regulator 51.

A base of the transistor 53 is electrically connected to an output terminal of the operational amplifier 52, an emitter of the transistor 53 is electrically connected to one end of the variable resistor 54, a collector of the transistor 53 is electrically connected to one end of the cable 24 connected to a cathode of the LEDS 9b. Another end of the variable resistor 54 is electrically connected to one end of the fixed resistor 55, and another end of the fixed resistor 55 is connected to the ground. In order to compensate for the variation in potential difference between the base and the emitter of the transistor 53 due to the temperature, the emitter is connected to a negative input terminal of the operational amplifier 52. A regulator driving power supply 56 of the power supply circuit 19 supplies power to the regulator 51. An operational-amplifier driving power supply 57 of the power supply circuit 19 supplies a voltage to the operational amplifier 52. Anodes of the LEDs 9b are connected to an LED driving power supply 58 of the power supply circuit 19. Then, the variable resistor 54 adjusts the amount of current flowing in the LEDs 9b to be constant. The fixed resistor 55 prevents the overflow of current to the LEDs 9b so as to determine the maximum level of current flowing to the LEDs 9b.

The user inputs the signal for controlling the turn-on of the LEDs 9b from the second user interface 21 and the system control unit 23 then outputs the signal for controlling the turn-on of the LEDs 9b to the LED control unit 15 in accordance with the signal inputted from the second user interface 21. The LED control unit 15 receives the signal for controlling the turn-on of the LEDS 9b from the system control unit 23, thereby switching on the regulator 51 of the constant-current circuit 15a. Further, the current flows to the base of the transistor 53 via the operational amplifier 52 from the regulator 51, thereby switching on the transistor 53. When the transistor 53 is turned on, the voltage is supplied to the LEDs 9b from the LED driving power supply 58, thereby turning-on the LEDs 9b. The amount of current flowing the LEDs forming the LEDs 9b is controlled be constant by the variable resistor 54 and the fixed resistor 55. That is, the variable resistor 54 presets, to be constant, the amount of current of the LEDs 9b, and the fixed resistor 55 presets the maximum amount of current flowing to the LEDs 9b. Therefore, it is possible to prevent the flow of excessively high current and excessively low current to the LEDs 9b.

When the user inputs the signal for controlling the turn-off operation of the LEDs from the second user interface 21, the system control unit 23 outputs the signal for controlling the turn-off of the LEDs 9b to the LED control unit 15 in accordance with the signal inputted from the second user interface 21. The LED control unit 15 receives the signal for controlling the turn-off of the LEDs 9b from the system control unit 23, then, the regulator 51 of the constant-current circuit 15a is turned off, and the current does not flow to the base of the transistor 53 via the operational amplifier 52 from the regulator 51, thereby turning off the transistor 53. Then, since the LED driving power supply 58 does not supply the voltage to the LEDs 9b and, therefore, the LEDs 9b are turned off.

A description is given of the case of attaching the interchangeable optical adaptor 8b to the distal end of the insertion unit 2. Upon attaching the interchangeable optical adaptor 8a or 8c, the same structure is obtained by replacing the LEDs 9b with the LEDs 9a or LEDs 9c. The same turn-on and turn-off operations as those of the LEDs 9b are performed. The LEDs 9a to 9c have varied voltages between the terminals in accordance with the characteristic between the forward-current/forward-voltage (hereinafter, referred to as a $V_F$ characteristic). However, the LED driving power supply 58 sufficiently supplies voltages to the LEDs 9a to 9c and, thus, the transistor 53 absorbs the variation in voltage between the terminals of the LEDs 9a to 9c depending on the $V_F$ characteristics. That is, the regulator 51, the operational amplifier 52, the transistor 53, the variable resistor 54, and the fixed resistor 55 form a constant-current driving circuit. When the LED driving power supply 58 sufficiently supplies the voltage, the amount of current flowing to each LED of the LEDs 9a to 9c is determined depending on the resistance between the variable resistor 54 and the fixed resistor 55 and a voltage value inputted to a positive input terminal of the operational amplifier 52 by the regulator 51. Therefore, upon attaching any of the interchangeable optical adaptors 8a to 8c to the distal end of the insertion unit 2, the amount of current flowing to the LEDs 9a to 9c with varied $V_F$ characteristics is constant. Further, it is possible to prevent the flow of excessively high current and excessively low current to the LEDs 9a to 9c.

In the electronic endoscope system according to the embodiment of the present invention, the number of parallel connections of the LEDs 9a to 9c included in the interchangeable optical adaptors 8a to 8c is commonly two arrays. Upon attaching any of the interchangeable optical adaptors 8a to 8c to the distal end of the insertion unit 2, the constant-current circuit 15a arranged to the LED control unit 15 drives the LEDs 9a to 9c, thereby omitting driving circuits dedicated for the interchangeable optical adaptors 8a to 8c and circuits and operations for switching the driving circuits. The operability is improved without the size increase in system. Further, upon attaching any of the interchangeable optical adaptors 8a to 8c to the distal end of the insertion unit 2, the constant-current circuit 15a arranged to the LED control unit 15 flows a constant amount of current to each LED of the LEDs 9a to 9c and the best amount of light for observation is always kept, thereby improving the observing property.

The electronic endoscope system 1 according to the embodiment of the present invention has the two user interfaces of the first user interface 13 and the second user interface 21 and the functions of the two user interfaces may be exchanged. For example, the second user interface 21 does not instruct the turn-on and the turn-off of the LEDs but the first user interface 13 may instruct them. Further, the functions of the first user interface 13 and the second user interface 21 may be integrated, thereby structuring the two user interfaces as one user interface. Furthermore, the integrated user interfaces may be divided into three or more user interfaces, thereby distributing the functions.

Figure 4:
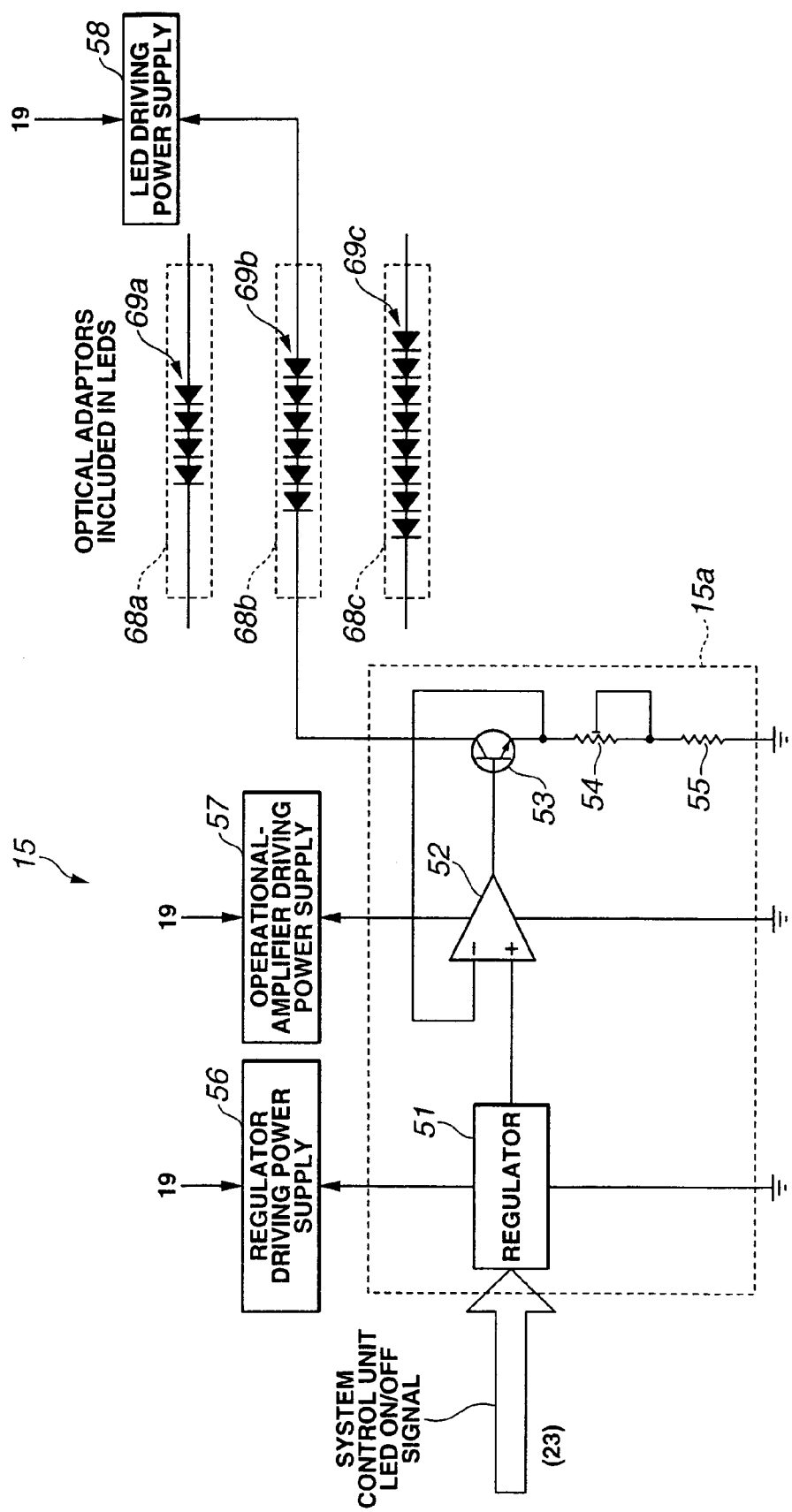
FIG. 4 is a circuit diagram for explaining another structure of the LEDs.

Although the number of parallel connections of the LEDs 9a to 9c are commonly two arrays, referring to FIG. 4, four, six, and eight LEDs may serially be connected, thereby forming LEDs 69a to 69c as one array. FIG. 4 is a circuit diagram for explaining another structure of the LEDs. Referring to FIG. 4, interchangeable optical adaptors 68a to 68c having the LEDs 69a to 69c can be attached to the distal end of the insertion unit 2 and can be used only by changing the variable resistor 54 in FIG. 4 to a resistance corresponding to the LEDs 69a to 69c as one array, without changing the structure of the constant-current circuit 15a of the LED control unit 15. In this case, the LEDs 69a to 69c have varied voltages between the terminals in accordance with the $V_F$ characteristics. However, the LED driving power supply 58 sufficiently supplies voltages to the LEDs 69a to 69c and, thus, the transistor 53 absorbs the variation in voltage between the terminals of the LEDs 69a to 69c depending on the $V_F$ characteristics.

Figure 5:
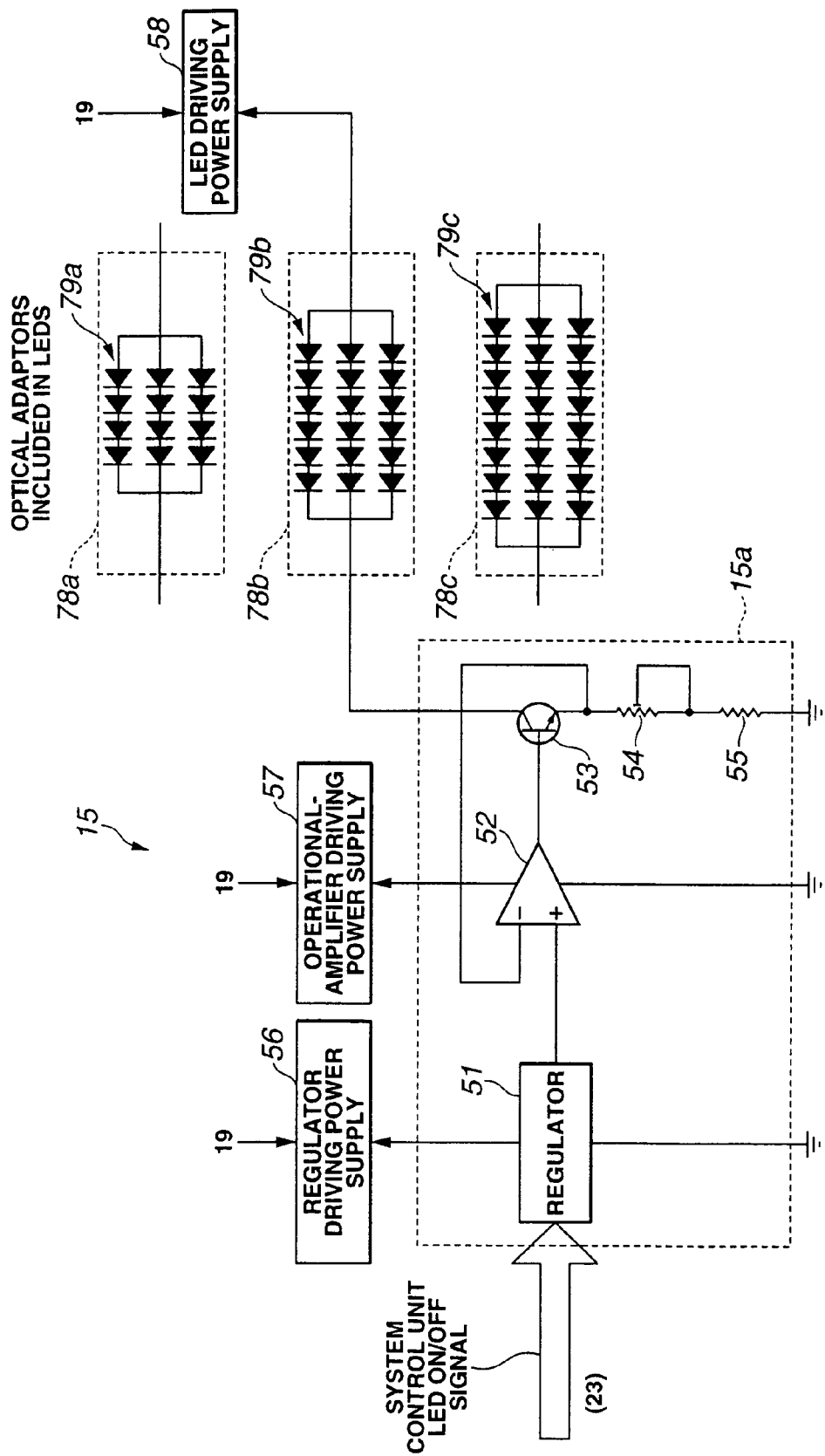
FIG. 5 is a circuit diagram for explaining another structure of the LEDs.

Referring to FIG. 5, three arrays of serial connection of four, six, and eight LEDs may be connected in parallel with each other, thereby forming LEDS 79a to 79c. FIG. 5 is a circuit diagram for explaining another structure of the LEDs. Referring to FIG. 5, interchangeable optical adaptors 78a to 78c having the LEDS 79a to 79c can be attached to the distal end of the insertion unit 2 and can be used only by changing the variable resistor 54 in FIG. 5 to a resistance corresponding to the LEDs 79a to 79c as three arrays, without changing the structure of the constant-current circuit 15a of the LED control unit 15. In this case, the LEDs 79a to 79c have varied voltages between the terminals in accordance with the $V_F$ characteristics. However, the LED driving power supply 58 sufficiently supplies voltages to the LEDs 79a to 79c and, thus, the transistor 53 absorbs the variation in voltage between the terminals of the LEDs 79a to 79c depending on the $V_F$ characteristics. When the number of parallel connections is common, the structure of four or more arrays can be realized.

In the LEDs 9a to 9c shown in FIGS. 2A to 2C, the numbers of serial connections of LEDs are four, six, and eight, however, the present invention is not limited to this. If the number of parallel connections is commonly two, the LEDs may the difference of one or more number of serial connections. Similarly to the LEDs 69a to 69c shown in FIG. 4 and the LEDs 79a to 79c shown in FIG. 5, if the number of parallel connections of LEDs is common, the LEDs may have the difference of one or more number of serial connections.

As mentioned above, according to the present invention, when a plurality of interchangeable optical adaptors having varied number of LEDs are used and the interchangeable optical adaptor is exchanged, the current flowing to each LED is the same and the excessively high current or excessively high voltage is not applied to the LEDs. Therefore, even when the interchangeable optical adaptor is exchanged, respective LEDs are properly and automatically driven. Therefore, the electronic endoscope system is realized with high operability and high observing property.

According to the embodiment, in the case of using a plurality of interchangeable optical adaptors having different numbers of light-emitting elements, the light-emitting element is properly and automatically driven without the size increase in system. Thus, the electronic endoscope system is realized with high operability and high observing property.

According to the embodiment, the power supply circuit 19 supplies the entire voltages supplied from the regulator driving power supply 56, the operational amplifier driving power supply 57, and the LED driving power supply 58. However, the present invention is not limited to this and the voltages supplied from the regulator driving power supply 56, the operational amplifier driving power supply 57, and the LED driving power supply 58 may be supplied from other power supplies, independent of the power supply circuit 19.

Figure 6:
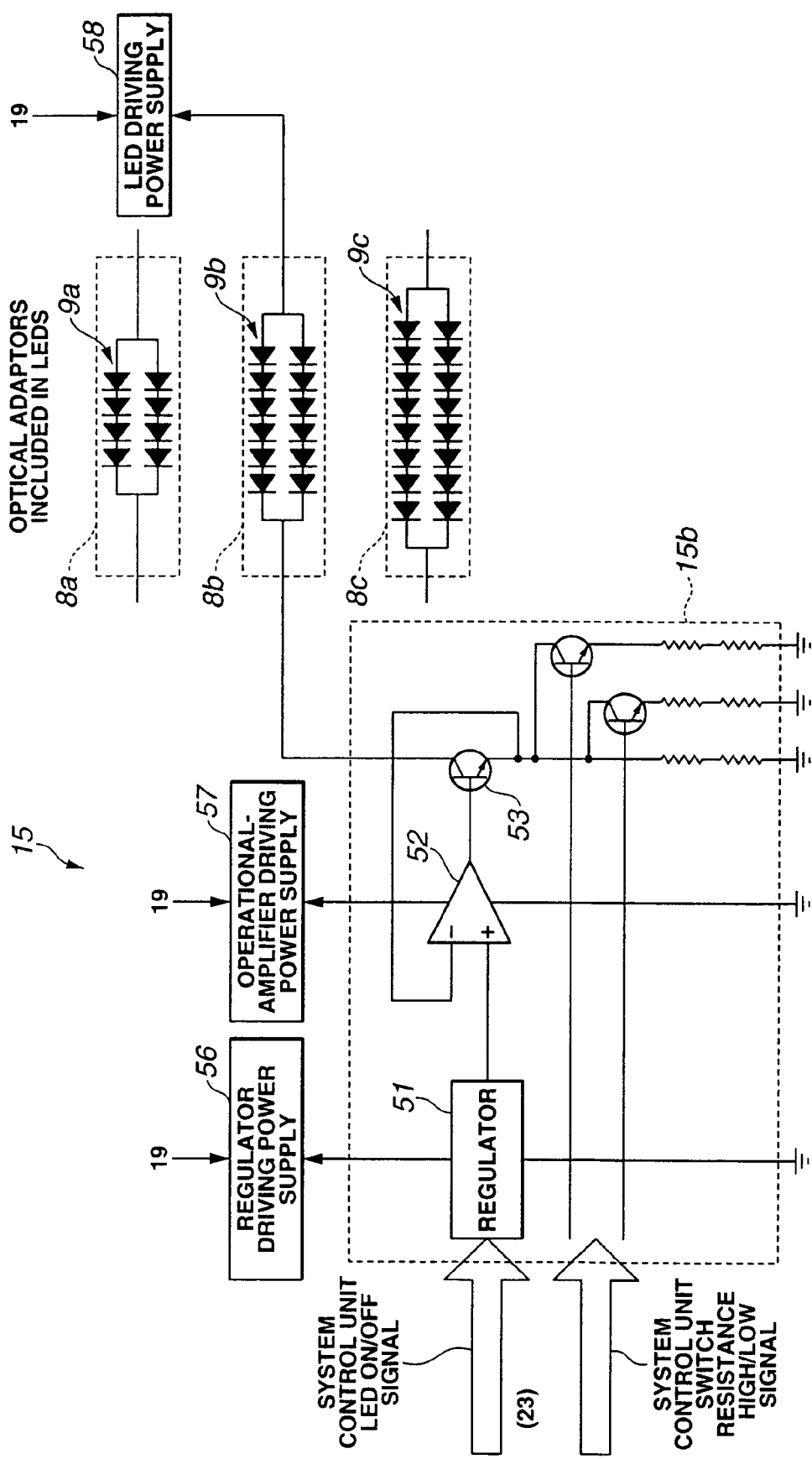
FIG. 6 is a circuit diagram for explaining another structure of the LED control unit.

Further, the constant-current circuit 15a of the LED control unit 15 changes the resistance of the variable resistor 54 in accordance with the number of parallel connections of the interchangeable optical adaptors, however, the present invention is not limited to this. As the constant-current circuit 15b shown in FIG. 6, a plurality of fixed resistors may be arranged in advance in accordance with the number of parallel connections of the interchangeable optical adaptors and may be exchanged by a switch in accordance with the number of parallel connections of the interchangeable optical adaptors to be used. Alternatively, the system control unit 23 may control the exchange operation of an electronic volume in accordance with the number of parallel connections of the interchangeable optical adaptors.

The present invention is not limited to the embodiment and can variously be changed and modified without departing from the essentials of the present invention.

What is claimed is:

1. An electronic endoscope system comprising:
   a plurality of optical adaptors, each optical adaptor having at least two arrays of serially connected light-emitting elements serving as illuminating means;
   an insertion unit to which one of the optical adaptors is freely detachably attached at a distal portion thereof, the one of the optical adaptors being configured to be replaceable with another optical adaptor, the insertion unit including an electric cable inserted thereto and connected to the light-emitting elements; and
   a control unit having a constant-current circuit that sets, to be constant, the amount of current flowing to the light-emitting element via the electric cable,
   wherein the constant-current circuit includes
      a resistor having one end connected to the light-emitting elements and another end connected to a ground,
      a transistor connected between the resistor and the light-emitting elements, and
      an operational amplifier, a connecting point between the transistor and the resistor being connected to a negative input terminal of the operational amplifier, and
   wherein the constant-current circuit sets to be constant the amount of current flowing to the light-emitting elements in accordance with an amount of voltage inputted to a positive input terminal of the operational amplifier.

2. An electronic endoscope system according to claim 1, wherein a number of the serially-connected light-emitting elements is the same in all the arrays.

3. An electronic endoscope system according to claim 2, wherein the plurality of optical adaptors have the same number of arrays of the light-emitting elements.

4. An electronic endoscope system according to claim 3, wherein the light-emitting element is a light-emitting diode.

5. An electronic endoscope system according to claim 2, wherein the light-emitting element is a light-emitting diode.

6. An electronic endoscope system according to claim 1, wherein the constant-current circuit of the control unit arbitrarily exchanges the amount of current in accordance with the plurality of optical adaptors.

7. An electronic endoscope system according to claim 1, wherein the light-emitting element is a light-emitting diode.

8. An electronic endoscope system comprising:
   an insertion unit;
   an optical adaptor detachably attached to a distal end of the insertion unit, the optical adaptor having at least two arrays of serially-connected light-emitting elements for illumination, the optical adaptor being configured to be replaceable with another optical adaptor having at least two arrays of serially-connected light-emitting elements; and
   a constant-current circuit that sets, to a constant amount of current, current to the light-emitting element via an electric cable inserted in the insertion unit,
   wherein the constant-current circuit includes
      a resistor having one end connected to the light-emitting elements and another end connected to a ground,
      a transistor connected between the resistor and the light-emitting elements, and
      an operational amplifier, a connecting point between the transistor and the resistor being connected to a negative input terminal of the operational amplifier, and
   wherein the constant-current circuit sets to be constant the amount of current flowing to the light-emitting elements in accordance with an amount of voltage inputted to a positive input terminal of the operational amplifier.

9. An electronic endoscope system according to claim 8, further comprising: a user interface unit that receives instructions for turn-on and turn-off of the light-emitting element, wherein the constant-current circuit controls the amount of current in accordance with the instruction for turn-on/turn-off operation inputted to the user interface unit.

* * * * *

UNITED STATES PATENT AND TRADEMARK OFFICE
CERTIFICATE OF CORRECTION

PATENT NO. : 7,599,734 B2
APPLICATION NO. : 11/188918
DATED : October 6, 2009
INVENTOR(S) : Masato Naruse It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1107 days.

Signed and Sealed this

Twenty-eighth Day of September, 2010

David J. Kappos
*Director of the United States Patent and Trademark Office*